United States Patent [19]

Leonard

[11] 4,299,981
[45] Nov. 10, 1981

[54] PREPARATION OF FORMIC ACID BY HYDROLYSIS OF METHYL FORMATE

[76] Inventor: Jackson D. Leonard, 7002 Blvd. East, Guttenberg, N.J. 07093

[21] Appl. No.: 912,189

[22] Filed: Jun. 5, 1978

[51] Int. Cl.$^3$ .................. C07C 27/00; C07C 51/09; C07C 53/02

[52] U.S. Cl. .................. 562/609; 203/77; 203/80; 203/88; 568/877; 568/913

[58] Field of Search .............. 562/609; 568/877, 913; 203/80, 77, 88

[56] References Cited

U.S. PATENT DOCUMENTS

| | | | |
|---|---|---|---|
| 2,160,064 | 5/1939 | Eversole | 562/609 |
| 3,907,884 | 9/1975 | Lynn et al. | 562/609 |

Primary Examiner—Vivian Garner
Attorney, Agent, or Firm—Bert J. Lewen; Paul H. Ginsburg

[57] ABSTRACT

Formic acid is produced in a continuous process by hydrolyzing methyl formate with water at high temperature and pressure in the presence of a formic acid catalyst. Methanol is also formed. The reesterification of the reaction products to methyl formate (a reaction favored by high temperatures) is minimized by flashing the reaction product at relatively low pressure and temperature and thereafter distilling the residual liquid under vacuum. This procedure separates the methyl alcohol from the formic acid with a minimum contact time and at a low temperature which does not favor the reesterification reaction. The flashed vapor, primarily unreacted methyl formate, is recycled to the reaction zone. High purity formic acid, i.e., 85%, is obtained by subjecting the bottom from the vacuum distillation to a second distillation step. The distillate from the vacuum distillation is distilled to separate residual methyl formate for recycle from the co-product methyl alcohol.

In another embodiment of the invention, prior to the main hydrolysis, the methyl formate is partially hydrolyzed to form the small amount of formic acid needed to accelerate the main hydrolysis step. Accordingly, the necessary formic acid catalyst is formed eliminating the need to recycle product formic acid.

4 Claims, 1 Drawing Figure

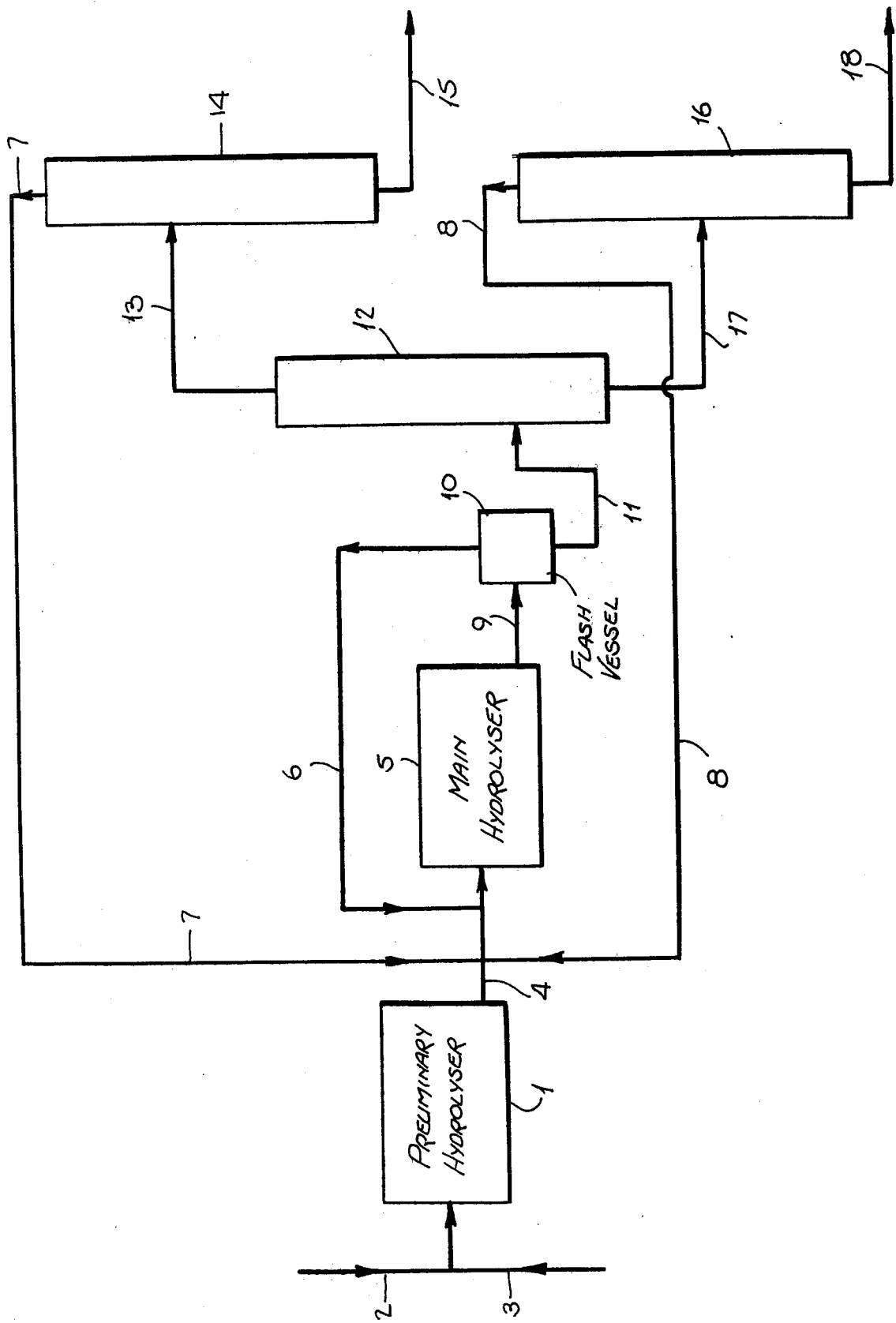

PREPARATION OF FORMIC ACID BY HYDROLYSIS OF METHYL FORMATE

BACKGROUND OF THE INVENTION

The formation of formic acid by the hydrolysis of alkyl formates is well-known in the art. The major drawback of such processes from the commercial standpoint is that the chemical equilibrium of the hydrolysis reaction does not favor the rapid formation of substantial amounts of formic acid. Even with mineral acid catalyst and high temperatures, the extended residence time necessary to reach equilibrium makes the process very complicated and expensive. Examples of such processes are shown in U.S. Pat. No. 2,160,064 and British Pat. No. 628,656. Though the use of the mineral acid catalyst did reduce reaction time, it created problems because of its tendency to promote the decomposition of the formic acid to carbon monoxide and water.

In recent years, the trend has been to perform the hydrolysis by using formic acid itself as the catalyst. While this overcame certain of the decomposition problems caused by the use of a strong mineral acid, the formic acid is less effective in accelerating the reaction.

To overcome this problem, U.S. Pat. No. 3,907,884 proposed the use of a solvent system to reduce the reaction equilibrium time at temperatures from 25° to 150° C. This process, however, while it serves to increase the reaction rate, is not fully effective because the reactants during purification tend to undergo a reverse reaction, that is, the formic acid and the methyl alcohol present in high concentrations and at high temperatures reesterified to reform substantial quantities to the methyl formate.

Another deficiency with the process taught in U.S. Pat. No. 3,907,884 is that it proposes adding the formic acid catalyst from an extraneous source. Obviously, this procedure results in decreasing the net production of formic acid and effectively reducing the capacity of the equipment.

BRIEF SUMMARY OF THE INVENTION

The subject invention concerns a process for obtaining improved yields of formic acid by the hydrolysis of methyl formate. In the process the hydrolysis is carried out at an elevated temperature and pressure using a molar excess of the methyl formate. The reaction products, after equilibrium is reached, are passed to a low pressure zone wherein a substantial quantity of the unreacted methyl formate is instantaneously flashed overhead. The liquid in the flash zone is thereby quickly cooled and then passed directly to a vacuum distillation column, whereby the methyl alcohol and residual methyl formate are rapidly separated from the formic acid-water residue. Because the formic acid and the methanol formed in the reaction are in contact only briefly at a reduced temperature and because the methyl formate concentration is high during their contact, reesterification is almost negligible.

Additionally, in a preferred embodiment of the invention, methyl formate and water are introduced into a preliminary hydrolysis zone maintained at an elevated temperature and pressure. In this reactor, though no formic acid is added, the methyl formate is partially hydrolyzed to form sufficient formic acid to catalyze the main hydrolysis step. The partially hydrolyzed product from this preliminary step is combined with the recycled methyl formate and water so that the total feed to the main hydrolysis contains a molar excess of the methyl formate.

BRIEF DESCRIPTION OF THE DRAWING

The FIGURE illustrates a continuous process exemplifying a preferred embodiment of the invention for the production of 10,000 metric tons per year of formic acid.

DETAILED DESCRIPTION OF THE INVENTION

The present invention relates to the preparation of formic acid by the hydrolysis of the methyl formate in the presence of a formic acid catalyst. More specifically, the invention relates to a high pressure-high temperature continuous reaction autocatalyzed by formic acid, whereby the reaction product is processed so as to substantially eliminate the reesterification of the reaction products during purification. Reesterification is further suppressed by using a molar excess of methyl formate in the hydrolysis.

The formic acid catalyst required for the main hydrolysis is formed in a preliminary hydrolysis zone wherein methyl formate and a mixture of steam and water are introduced into a high temperature-high pressure zone. The main hydrolysis step of the instant invention is performed at a temperature 90° to 140° C. at pressures from 5 to 18 atmospheres, in the liquid phase at a methyl formate-water molar ratio of from 1.5:1 to 10:1, preferably from 2:1 to 4:1. Under these conditions the reactants are in a single phase. This eliminates the necessity of employing a solvent sytem as proposed by U.S. Pat. No. 3,907,884. While methyl alcohol may be present because of its formation in the hydrolysis, the addition of a solvent is not beneficial to the instant process. A molar excess of the methyl formate drives the reaction in the desired direction.

The products from the main hydrolysis reactor are passed directly to a low pressure zone maintained at a pressure of from about 2 atmospheres to 700 mm. Hg, preferably at atmospheric pressure. This zone serves to rapidly cool the products of reaction and reduce the quantities of material which need be subject to distillation. The liquid from the low pressure zone is fed directly into a vacuum distillation column maintained at a pressure of from 10 to 700 mm Hg wherein the methyl alcohol, as well as residual methyl formate, is rapidly separated from the formic acid and water. Naturally, once the methyl alcohol and the formic acid are separated the reesterification cannot occur. On the other hand, without the low pressure flashing step, the residence time required in the vacuum distillation would have to be substantially longer, since considerably more material would have to be distilled in the packed column. This flashing procedure also permits the economical operation of the hydrolysis reactor with a stoichiometric excess of the methyl formate (a condition which improves the amount of formic acid produced and minimizes reesterification) without over-loading the distillation capacity of the system. In the flashing step a substantial amount of the unreacted methyl formate is vaporized and separated, i.e., at least 25%, preferably at least 50% of the total leaving the main hydrolyzer.

In another embodiment of the invention, prior to the main hydrolysis, a portion of the methyl formate and a steam-water mixture is fed to a preliminary hydrolysis reactor maintained at elevated temperatures and pressure. This reactor is operated at similar conditions to the main hydrolyzer, namely, at temperatures of from 90° to 140° C. and pressures from 5 to 18 atmospheres. Generally lower pressures may be used because of the lower volatility of the reactants. The methyl formate-water molar ratio is from 0.5:1 to 3:1. Though no formic acid is added to the preliminary hydrolyzer, sufficient hydrolysis takes place to form sufficient formic acid to catalyse the main hydrolysis reaction. In this latter reaction zone, the contents from the preliminary reactor are combined with the methyl formate and water recycled from the distillation columns. This embodiment is of significant economic advantage because it eliminates the need for recycling purified formic acid or the addition of extraneous formic acid to the process. Since the preliminary hydrolyzer is an inexpensive addition to the overall process, this technique of forming the necessary formic acid for catalysis is particularly advantageous. In this embodiment of the invention the recycle methyl formate constitutes from 60 to 95% of the methyl formate added to the main hydrolyzer, preferably 75 to 90%.

Turning now to the FIGURE, in the continuous process, the quantities given are pounds per hour. For simplicity only "parts" shall be referred to.

Via lines 2 and 3, 3078 parts of methyl formate and 1340 parts of steam and water are fed to the preliminary hydrolyzer 1. The preliminary hydrolyzer 1 is a glass-lined pipe reactor maintained at a pressure of 10 atm. and a temperature of 120° C. This represents a molar ratio of methyl formate to water of about 0.7:1.

In the preliminary hydrolyzer 1,460 parts of formic acid, 320 parts of methanol and the 1160 parts of water are formed. About 2478 parts of methyl formate remain unreacted. The effluent is fed via line 4 into the main hydrolyzer 5 along with the recycle streams 6, 7 and 8. These have the following compositions:

| LINE NO. | METHYL FORMATE | WATER | FORMIC ACID | METHYL ALCOHOL |
| --- | --- | --- | --- | --- |
| 4 | 2478 | 1160 | 460 | 320 |
| 6 | 6088 | 62 | 285 | 372 |
| 7 | 10028 | — | — | — |
| 8 | — | 1118 | — | — |
| TOTAL | 18594 | 2340 | 745 | 692 |

The total feed to the main hydrolyzer 5 has a methyl formate/water mol ratio of 2.4:1. This reactor is maintained at a temperature of 120° C. and a pressure of about 9 atm. As will be understood by those skilled in the art, the formic acid formed in the preliminary hydrolyzer 1 serves as the catalyst for the reaction in the main hydrolyzer 5. Because of the severe conditions of temperature and pressure, the hydrolysis reaction achieves 95% equilibrium in approximately 20 seconds.

The reaction product from the main hydrolyzer 5 contains 2645 parts of formic acid, 2013 parts of methyl alcohol, 16,116 parts of methyl formate and 1597 parts of water, and passes via line 9 to flash vessel 10. The latter is maintained at atmospheric pressure. In the flash vessel 10 a substantial portion of the unreacted methyl formate, namely 6088 parts, flashes off via line 6 rapidly cooling the remaining liquid. The vapor is recycled to the main hydrolyzer 5. The liquid passes via line 11 to the first distillation column 12, a glass-lined steel column packed with woven glass mats containing only sufficient volume to minimize liquids hold-up. The distillation column 12 is maintained at 400 mm Hg pressure and at a bottoms temperature of about 80° C. The temperature of the distillate leaving the column is approximately 22° C. and the reflux ratio about 0.6 to 1. The flashing off of the substantial amount of methyl formate in the flash vessel 10 permits the operation of the distillation column 12 at low reflux, at a reduced temperature and with a minimum of contact time. Accordingly, there is negligible reesterification, i.e., less than 0.1%, of the formic acid and methanol. In contrast, if the flashing step is eliminated, about 20% of the formic acid fed to the first distillation column reesterifies. Additionally, the low temperature minimizes corrosion problems.

The distillate from the column 12, containing 10,028 parts of methyl formate and 1641 parts of methyl alcohol, passes via line 13 to the second distillation column 14. This column 14 operates at 1.7 atm., a bottoms temperature of about 77° C. and a distillate temperature of 50° C. It is also glass-lined and packed with glass mates. Substantially pure methanol (1641 parts) is taken off as the residue and sent to storage via line 15. The overhead methyl formate is recycled via line 7 to the main hydrolyzer 5.

The residue, 2360 parts of formic acid and 1535 parts of water, from the first column 12 is fed to a third glass-lined distillation column 16 via line 17. The third distillation column 16 is packed with glass mats and operated at about 2.6 atms., a bottom temperature of 142° C., and a distillate temperature of 131° C. is maintained. The overhead stream, consisting essentially of water, is recycled via line 8 to the main hydrolyzer 5. The residue is removed via line 18, and consists of 2360 parts of formic acid and 417 parts of water, i.e., 85% formic acid.

It should be understood that the foregoing description is merely an exemplification of the subject invention and that many variations may be made without departing from the spirit of the invention.

What is claimed is:

1. A process for the preparation of formic acid by the liquid phase hydrolysis of methyl formate which comprises: passing methyl formate and water to a reaction zone maintained at a pressure of from 5 to 18 atms. and a temperature of 90° to 140° C., the molar ratio of said methyl formate to water being from 1.5:1 to 10:1; providing sufficient reactor volume to allow the hydrolysis to reach at least 95% of equilibrium; discharging the resultant product into a low pressure zone maintained at a pressure of from about 2 atmospheres to 700 mm. Hg, wherein a substantial quantity of the unreacted methyl formate is vaporized overhead and the remaining liquid is thereby quickly cooled; feeding the liquid from said low pressure zone to a distillation zone maintained at a pressure of from 10 to 700 mm. Hg; and separating the residual unreached methyl formate and methyl alcohol as a distillate from said distillation zone and a water-formic acid stream as a residue from said distillation zone.

2. A process for the preparation of formic acid by the liquid phase hydrolysis of methyl formate which comprises: passing methyl formate, water and steam to a preliminary hydrolyzer maintained at a pressure from 5 to 18 atms. and a temperature of from 90° to 140° C., the molar ratio of methyl formate and water in said preliminary hydrolyzer being from 0.5:1 to 3:1; partially hydrolyzing the methyl formate to form catalytic quantities of formic acid; passing the effluent directly to a main hydrolyzer; adding to said main hydrolyzer additional methyl formate and water so that the methyl formate-water molar ratio to the main hydrolyzer is from 1.5:1 to 10:1; maintaining said main hydrolyzer at a pressure of from 5 to 18 atms. and a temperature of from 90° to 140° C.; further hydrolyzing said methyl formate until equilibrium conditions are reached; discharging the resultant product into a low pressure zone maintained at a pressure of from about 2 atmospheres to 700 mm. Hg, wherein a substantial quantity of the unreacted methyl formate is vaporized overhead and the remaining liquid is thereby quickly cooled; separating the formic acid, methyl alcohol, unreacted methyl formate and water from the remaining liquid in the low pressure zone by vacuum distillation and recycling of the separated unreacted methyl formate and water to said main hydrolyzer.

3. The process of claim 1 or 2, wherein the low pressure zone is maintained at about atmospheric pressure.

4. The process of claim 2, wherein the vacuum distillation is performed at a pressure of from 10 to 700 mm. Hg.

* * * * *